US00PP17627P2

(12) United States Plant Patent
Raser

(10) Patent No.: US PP17,627 P2
(45) Date of Patent: Apr. 17, 2007

(54) ***LAVANDULA* PLANT NAMED 'LAVANG 200'**

(50) Latin Name: *Lavandula angustifolia Mill.*
Varietal Denomination: Lavang 200

(75) Inventor: Gerald Raser, Vienna (AT)

(73) Assignee: Ernst Benary Samenzucht GmbH, Hann. Münden (DE)

( * ) Notice: Subject to any disclaimer, the term of this patent is extended or adjusted under 35 U.S.C. 154(b) by 0 days.

(21) Appl. No.: 11/251,148

(22) Filed: Oct. 14, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—The Webb Law Firm

(57) ABSTRACT

A new and distinct cultivar of *Lavandula* plant named 'Lavang 200', characterized by its vibrant deep blue colored flowers and its heat resistance.

3 Drawing Sheets

Botanical classification: *Lavandula angustifolia Mill.*
Varietal denomination: 'Lavang 200'.

BACKGROUND OF THE INVENTION

The present invention comprises a new and distinct cultivar of *Lavandula Angustifolia Mill.* known by the varietal name 'Lavang 200'. The new variety is a product of a planned breeding program conducted in Austria. The purpose of the breeding program was to develop new propagated generative cultivars. The new variety is the result of a cross of 'Munstead' (female parent) with pollen of unknown and different *Lavandula* varieties. The new variety is similar to its parent in flower height, but it has a deeper blue flower color. Asexual reproduction of the new cultivar in Austria by cuttings has shown that the unique features of the new variety are stable and reproduced true to type in successive propagations by asexual reproduction.

BRIEF DESCRIPTION OF THE DRAWINGS

The accompanying colored photographic drawings illustrate the new variety, with the colors being as nearly true as is possible to obtain in colored illustrations of this type.

DESCRIPTION OF THE PLANT

Figure 1:
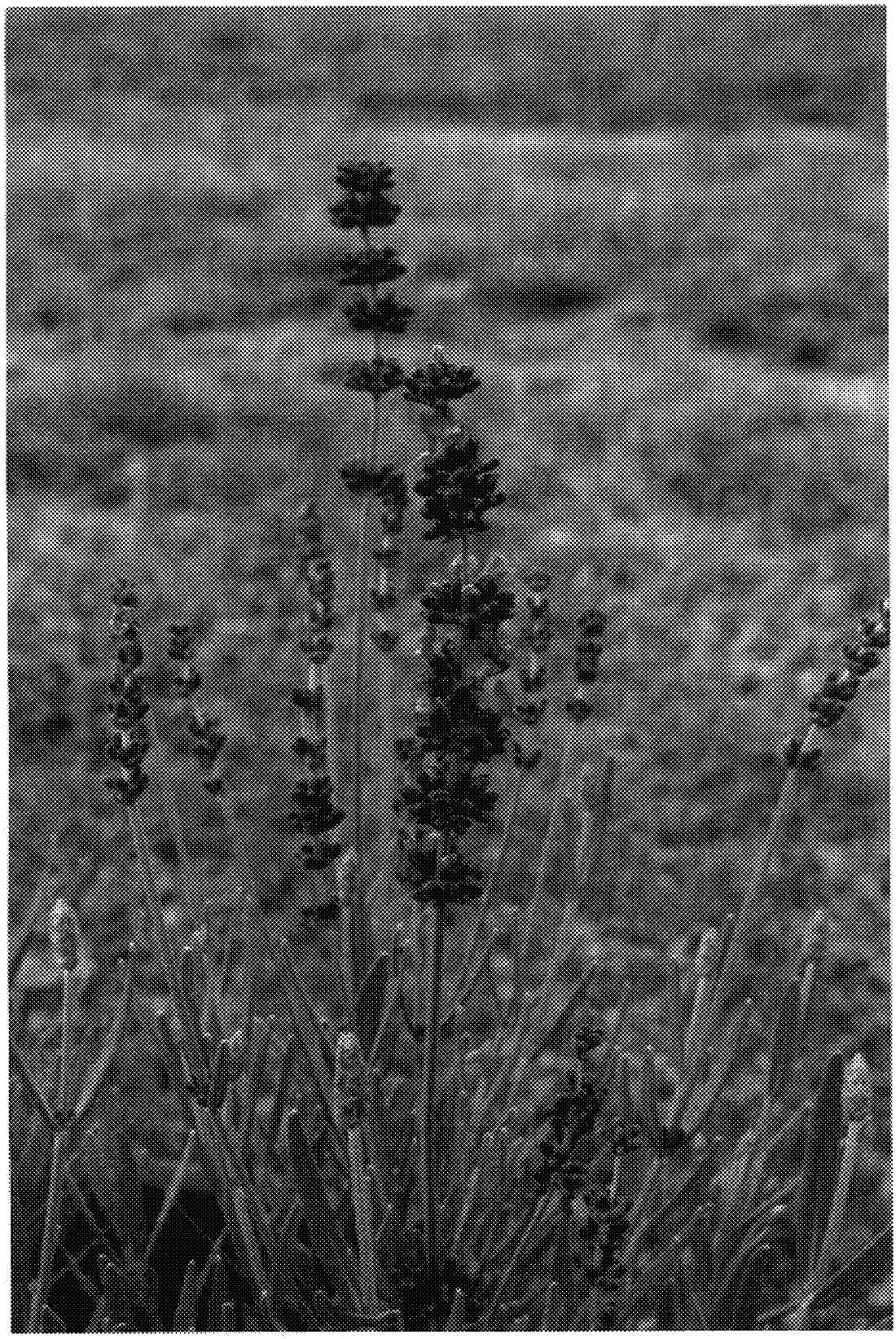
FIG. 1 is a close-up of the blooms of the new variety.
Figure 2:
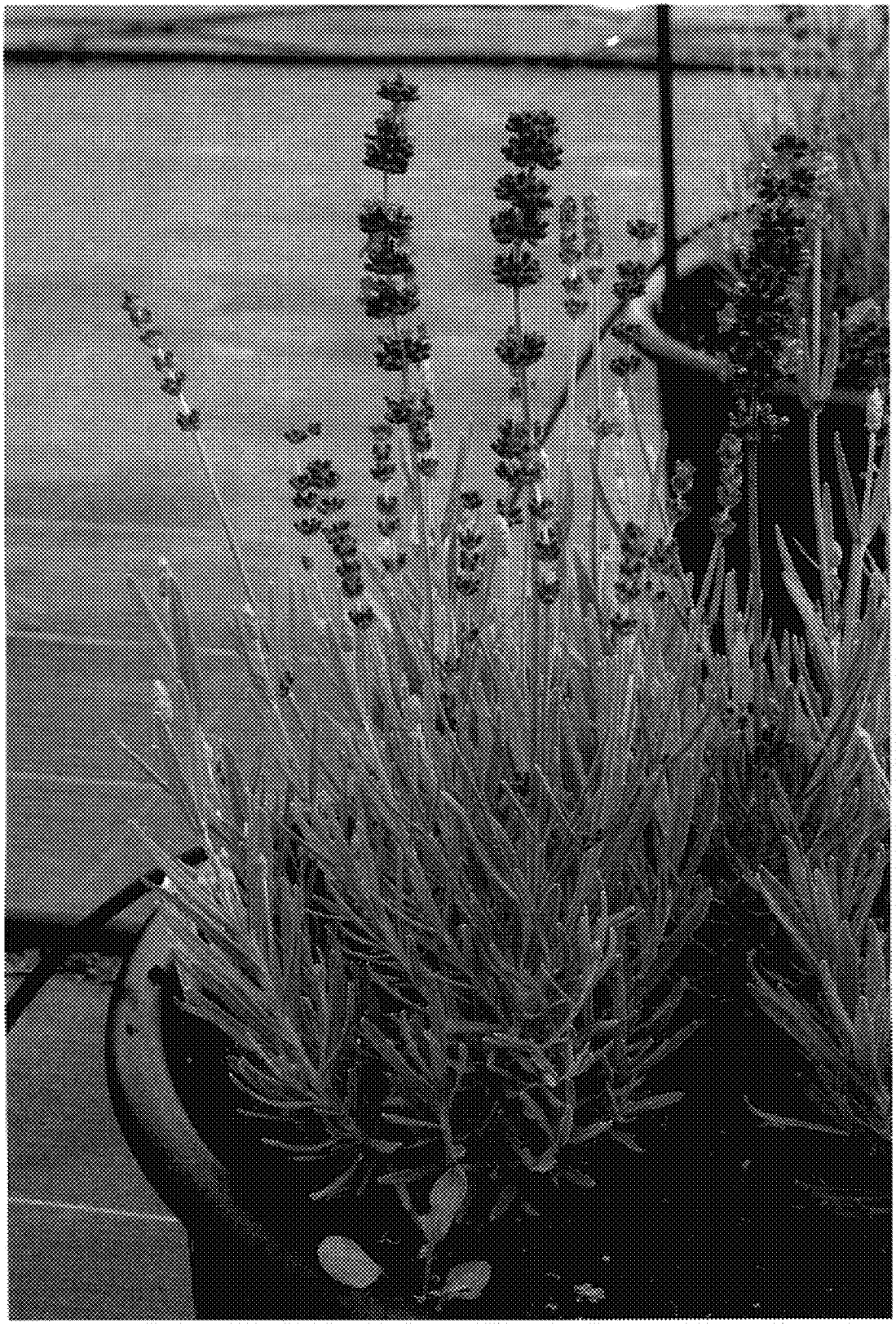
FIG. 2 illustrates an entire plant of the new variety.
Figure 3:
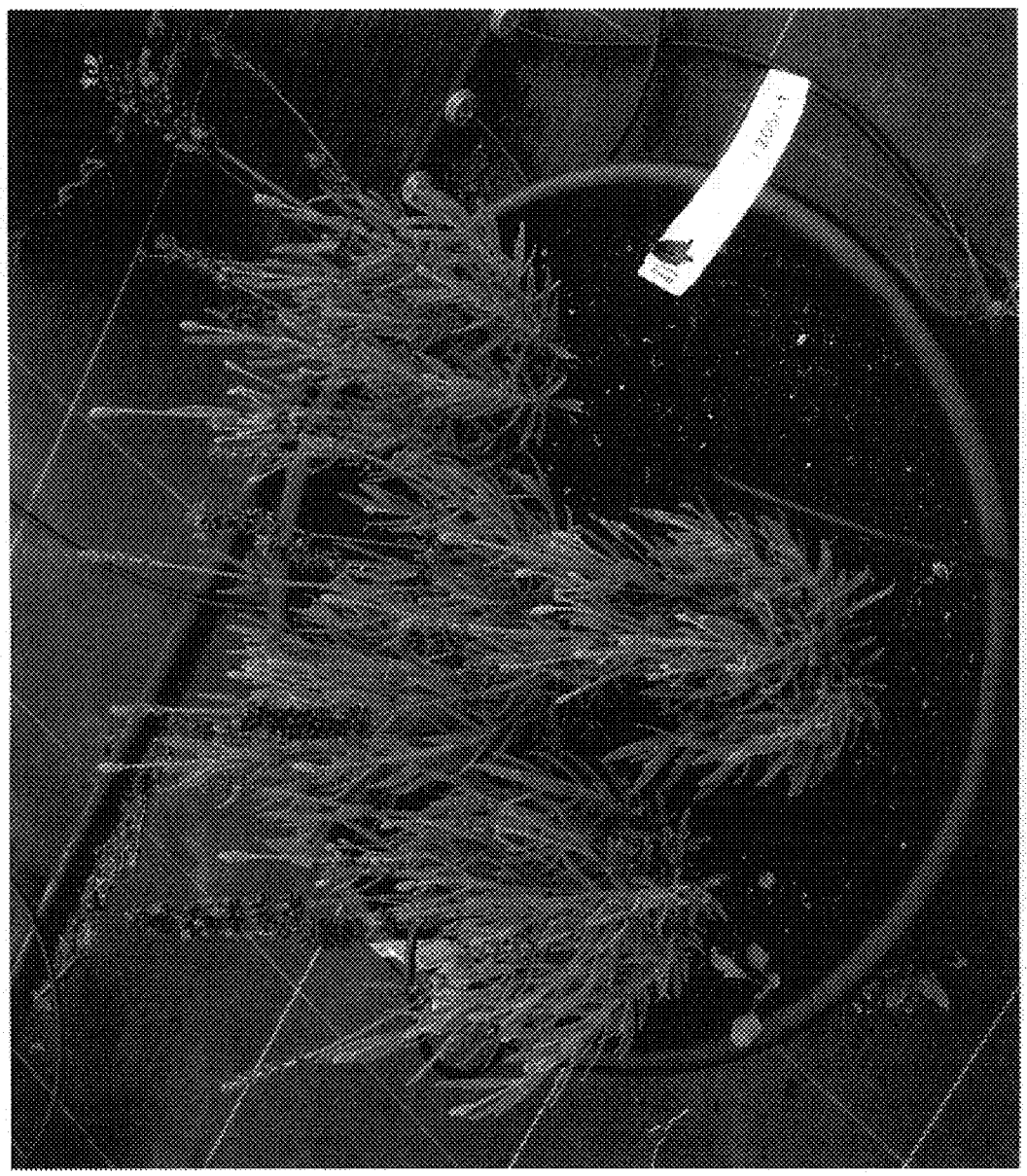
FIG. 3 shows multiple entire plants of the new variety.

The cultivar 'Lavang 200' has not been observed under all possible environmental conditions. The phenotype may vary somewhat with variations in environment such as temperature, day length and light intensity. However, there is no variance in genotype.

In the following description, color references are made to The Royal Horticultural Society Colour Chart, except where general terms of ordinary dictionary significance are used. Plants for the following description were grown in a 4" (~11 cm.) pot at approximately 64° F. The plant was 8 months old when described under natural light conditions in a greenhouse in Austria.

PLANT

Form: Bushy, symmetrical.
Height from soil to top of flowers: 14" (~35 cm.).
Plant diameter: 9" (~23 cm.).
Time to initiate roots: 3 weeks at approximately 68–72° F.
Time to produce a rooted plant: 8 weeks at approximately 64° F.
Vigor: Good.
Branching habit: Freely branching.
Stem:
- *Color.*—Green Group 138A.
- *Texture.*—Tender, with pubescence present.
- *Length.*—5" (~13 cm.).
- *Diameter.*—0.03 cm.
- *Internode length.*—0.05 cm.
- *Strength.*—Strong.
- *Quantity.*—Approximately 50 per plant.

Foliage:
- *Arrangement.*—Alternate.
- *Number of leaves per stem.*—12.
- *Size of leaf.*—Length: 2" (~5 cm.). Width: 0.05 cm.
- *Shape of leaf.*—Long and ligulate.
- *Shape of apex.*—Slender, long and tapered.
- *Shape of base.*—Slender.
- *Texture.*—Pubescent.
- *Margin type.*—Entire.
- *Fragrance.*—Present.
- *Color.*—Young leaves: Upper surface: Green Group 139C. Lower surface: Green Group 139C. Mature leaves: Upper surface: Green Group 139C. Lower surface: Green Group 139C.
- *Petiole.*—Not present — Sessile.
- *Veins.*—Venation pattern: One central vein. Color: Upper surface: Greyed-Green Group 189A. Lower surface: Green Group 139C.

FLOWER

Natural flowering season: June/July in Kittsee, Austria.
Flower type: Spike.
Number of flowers per plant: 50.
Time of day of flower opening: Flowers are open all day. They do not close.

Fragrance: Present and strong.
Longevity: 4 weeks on the plant.
Flower height: 1.2" (~3 cm.).
Flower diameter: 0.8" (~2 cm.).
Bud:
*Stage of development when described.*—At the beginning of flowering.
*Shape.*—Oval.
*Diameter.*—0.4" (~1 cm.).
*Length.*—1.2" (~3 cm.).
*Color.*—Violet Group 86A.
Corolla:
*Length.*—Upper lips: 0.04 cm. — 2 lips. Lower lips: 0.03 cm.
*Width.*—Upper lips: 0.07 cm. (2×3.5 mm.). Lower lips: 0.07 cm. (3×2.3 mm.).
*Shape.*—Upper lips: Rounded with 2 bigger petals. Lower lips: Rounded with 3 smaller petals.
*Apex.*—Upper lips: Two lappets, cut in. Lower lips: Three lappets, cut in.
*Margin.*—Upper lips: Smooth, round. Lower lips: Smooth, round.
*Texture.*—Upper lips: Velvety. Lower lips: Velvety.
*Color.*—When opening: Upper lips (upper and lower surfaces): Violet-Blue Group 90C. Lower lips (upper and lower surfaces): Violet-Blue Group 90C. Fully opened: Upper lips (upper and lower surfaces): Violet-Blue Group 93C, but having a lighter base of Violet-Blue Group 90D. Lower lips (upper and lower surfaces): Violet-Blue Group 93C, but having a lighter base of Violet-Blue Group 90D.
Calyx:
*Arrangement.*—Tube, in spike.
*Sepal.*—Length: 0.5 cm. Width: 0.03 cm. Shape: Oval and long. Margin: Hairy. Texture: Glazed. Color (when opening): Violet Group 86A. Color (fully opened): Violet Group 86A on top, Green Group 139D at the base.

Peduncle strength: Good.
Disease resistance: No susceptibility to disease noticed to date.
Weather tolerance: Heat tolerant, but susceptible to wet conditions.
Lasting quality of flowers:
*On plant.*—All summer.
*Of cut flowers.*—One day.
Seed:
*Number.*—Approximately 35 seeds per inflorescence.
*Texture.*—Polished.
*Color.*—Black.
*Length.*—0.03 cm.
*Diameter.*—0.01 cm.
Fruit:
*Texture.*—Velvety.
*Length.*—0.05 cm.
*Diameter.*—0.04 cm.
*Color.*—Brown Group 200A.

REPRODUCTIVE ORGANS

Stamens:
*Number per flower.*—4.
*Filament length.*—0.01 cm.
*Anthers.*—Shape: Long and slender. Length: 0.5 mm. Color: Yellow-White Group 158D.
*Pollen.*—Color: Greyed-Orange Group 164A. Amount: Minimal.
Pistils:
*Length.*—0.05 cm.
*Styles.*—Length: 0.01 cm. Color: Yellow-White Group 158D.
*Stigma color.*—Yellow-White Group 158D.

I claim:

1. A new and distinct variety of *Lavandula* plant named 'Lavang 200' as herein described and illustrated.

* * * * *

UNITED STATES PATENT AND TRADEMARK OFFICE

CERTIFICATE OF CORRECTION

PATENT NO. : PP 17,627 P2
APPLICATION NO. : 11/251148
DATED : April 17, 2007
INVENTOR(S) : Raser It is certified that error appears in the above-identified patent and that said Letters Patent is hereby corrected as shown below:

Column 1, Line 7, "*Angustifolia*" should read -- *angustifolia* --

Column 1, Line 12, "its parent" should read -- its female parent --

Signed and Sealed this

Third Day of July, 2007

JON W. DUDAS
*Director of the United States Patent and Trademark Office*